US00PP10029P

United States Patent [19]

Rother

[11] Patent Number: Plant 10,029

[45] Date of Patent: Sep. 16, 1997

54] PETUNIA PLANT NAMED SUNSTRIKER

76] Inventor: Reinhard W. Rother, 56 Emerald Monbulk Road, Emerald, Victoria 3782, Australia 21] Appl. No.: 680,165

22] Filed: Jul. 15, 1996

51] Int. Cl.[6] ..... A01H 5/00

52] U.S. Cl. ..... Plt./68.1

58] Field of Search ..... Plt./68.1

*Primary Examiner*—James R. Feyrer

*Attorney, Agent, or Firm*—C. A. Whealy

[57] ABSTRACT

A distinct cultivar of Petunia plant named 'Sunstriker', characterized by its medium purple petals with white/yellow green flower throat and tube; moderately vigorous growth habit and rapid growth rate; upright, but spreading plant habit; freely branching habit; early flowering; very floriferous with numerous flowers per plant; and tolerance to rain, drought and temperature extremes.

2 Drawing Sheets

1

The present invention relates to a new and distinct cultivar of Petunia plant, botanically known as *Petunia axillaris*, and hereinafter referred to by the cultivar name Sunstriker.

The new cultivar is a product of a planned breeding program conducted by the inventor in Emerald, Victoria, Australia. The objective of the breeding program was to create new Petunia cultivars having uniform plant habit and desirable flower colors.

The new cultivar originated from a cross made by the inventor of the Petunia cultivar Sweet Victory (disclosed in U.S. Plant Pat. No. 9,409) the male or pollen parent with the Petunia cultivar Sunkiss (not patented) as the female or seed parent.

The cultivar Sunstriker was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar Sunstriker has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Sunstriker'. These characteristics in combination distinguish 'Sunstriker' as a new and distinct cultivar:

1. Medium purple petals with white/yellow green flower throat and tube.
2. Moderately vigorous growth habit and rapid growth rate.
3. Upright, but spreading plant habit.
4. Freely branching habit. Plants do not require pinching.
5. Early flowering.
6. Very floriferous with numerous flowers per plant.
7. Tolerant to rain, drought and temperature extremes.

The cultivar Sunstriker is most similar in flower color to the cultivar Pampas Fire (disclosed in U.S. Pat. No. P.P.9,408). The cultivar differs from the cultivar Pampas Fire in the following characteristics:

1. Plants of the cultivar Sunstriker are more upright and less spreading than plants of the cultivar Pampas Fire.
2. Leaves of the cultivar Sunstriker are smaller than leaves of the cultivar Pampas Fire.
3. Leaves of the cultivar Sunstriker are elliptic in shape whereas leaves of the cultivar Pampas Fire are ovate in shape.

2

4. Leaves of the cultivar Sunstriker are more pubescent than leaves of the cultivar Pampas Fire.
5. Flowers are smaller on plants of the cultivar Sunstriker compared to plants of the cultivar Pampas Fire.
6. Plants of the cultivar Sunstriker have smaller sepals than plants of the cultivar Pampas Fire.
7. Pedicels of the cultivar Sunstriker are longer than pedicels of the cultivar Pampas Fire.
8. The flower throat and tube color of plants of the cultivar Sunstriker are yellow green whereas the flower throat and tube color of plants of the cultivar Pampas Fire are dark purple.
9. The flower throat and tube vein color of plants of the cultivar Sunstriker are purple, yellow green and yellow green, respectively, whereas the flower throat and tube vein color of plants of the cultivar Pampas Fire is purple.
10. The inside and outside petal colors of plants of the cultivar Sunstriker is lighter than the inside and outside petal colors of plants of the cultivar Pampas Fire.
11. The anther color of plants of the cultivar Sunstriker is cream whereas the anther color of plants of the cultivar Pampas Fire is purple.

A detailed comparison of the cultivars Sunstriker and Pampas Fire appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical hanging basket plant of the cultivar Sunstriker.

The second photograph comprises a close-up view of individual flowers of the cultivar Sunstriker. Flower and foliage colors may appear different than the actual colors due to light reflectance.

In the following description, color references are made to The Royal Horticultural Society Colour Chart except where general terms of ordinary dictionary significance are used. Measurements are averages from ten specimens selected at random from five plants.

Botanical classification: *Petunia axillaris* cultivar Sunstriker.

Parentage:

*Male or pollen parent.*—*Petunia axillaris* cultivar Sweet Victory (U.S. Plant Pat. No. 9,409).

*Female or seed parent.*—*Petunia axillaris* cultivar Sunkiss (not patented).

Propagation:

*Type cutting.*—Terminal vegetative cuttings.

*Time to initiate roots.*—About ten days at 21C soil temperature.

*Rooting habit.*—Numerous, fine, fibrous, and well-branched.

Plant description:

*Form.*—Indeterminate, upright, diffuse spreading, viscid, glandular pubescent.

*Branching habit.*—Freely branching.

*Plant height.*—About 24 cm.

*Plant width.*—About 46.8 cm.

*Vigor.*—Moderate.

*Crop time.*—Eight to nine weeks from a unrooted cutting to a 10.5-cm finished and flowering container.

*Foliage description.*—Leaves simple, generally symmetrical, sessile, and long persisting. Leaves at first whorled, later alternate, somewhat fleshy. Size (largest leaves): Length: About 7.4 cm. Width: About 3.5 cm. Thickness: About 1.5 min. Shape: Elliptic. Aspect: Horizontal to upright. Apex: Acute. Base: Attenuate. Margin: Entire. Texture: Moderately pubescent. Color: Young foliage upper side: 137A. Young foliage under side: 147B. Mature foliage upper side: 137A. Mature foliage under side: 147B.

*Stem description.*—Stems upright to spreading, hirsute. Stem diameter: About 3 min. Internode length: About 3.7 cm. Stem color: Green, 144A.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 6 cm. Height: About 4.9 cm. Flower tube width at distal end: Narrow, about 1.3 cm. Petal quantity: Five, fused. Petal apex: Acute. Margin: Entire. Texture: Pubescent on outside, smooth and satiny on inside. Color: Flower throat (inside): 150D. Flower throat vein color (inside): 144A. Flower tube color (outside): 150D. Flower tube vein color (outside): 144A. Petal color, inside: 74A. Petal vein color, inside: 74A. Petal color, outside: 75A to 75D. Petal vein color, outside: 144A.

*Sepals.*—Quantity: Five. Size: Length: About 1.9 cm. Width: About 4.4 min. Shape: Elliptic. Apex: Obtuse. Margin: Entire. Texture: Pubescent. Aspect: Upward to horizontal. Color: Inside: 144A. Outside: 144A.

*Pedicel.*—Aspect: Upright. Size: Length: About 3.8 cm. Width: Narrow, about 1.6 mm. Texture: Pubescent. Color: 144A.

*Reproductive organs.*—Stigma level or above anthers, superior ovary. Stamens: Stamen number: Five, four are didymous. Anther color: Cream. Filament color: Green white. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

CHART A

| CHARACTERISTIC | 'SUNSTRIKER' | 'PAMPAS FIRE' |
|---|---|---|
| PLANT HEIGHT | 24 cm | 14 cm |
| PLANT WIDTH | 46.8 cm | 75.6 cm |
| GROWTH HABIT | Upright to spreading | Spreading |
| LEAF LENGTH | 7.4 cm | 9.6 cm |
| LEAF WIDTH | 3.5 cm | 4.5 cm |
| LEAF SHAPE | Elliptic | Ovate |
| LEAF PUBESCENCE | Moderate | Sparse |
| COROLLA DIAMETER | 6 cm | 7.6 cm |
| COROLLA HEIGHT | 4.9 cm | 6 cm |
| FLOWER TUBE WIDTH | 1.3 cm | 1.6 cm |
| SEPAL LENGTH | 1.9 cm | 2.7 cm |
| SEAPL WIDTH | 4.4 mm | 7.3 mm |
| PEDICEL LENGTH | 3.8 cm | 2.5 cm |
| FLOWER THROAT COLOR | 150D | 83A |
| FLOWER THROAT VEIN COLOR | Yellow green | Purple |
| FLOWER TUBE COLOR | 150D | 83A |
| FLOWER TUBE VEIN COLOR | Yellow green | Purple |
| PETAL COLOR, INSIDE | 74A | Darker than 74A |
| PETAL VEIN COLOR, INSIDE | Red purple | Purple |
| PETAL COLOR, OUTSIDE | 75A to 75D | 80C |
| PETAL VEIN COLOR, OUTSIDE | Yellow green | Purple |
| PETAL LOBATION | Shallow | Medium |
| PETAL TIP | Obverse | Medium |
| PETAL WAVING | Weak | Medium |
| STIGMA RELATIVE TO ANTHERS | Level to above | Level |
| ANTHER COLOR | Cream | Violet |
| FILAMENT COLOR | Green white | Green white with violet towards anther |

It is claimed:

1. A new and distinct cultivar of Petunia plant named 'Sunstriker', as illustrated and described.

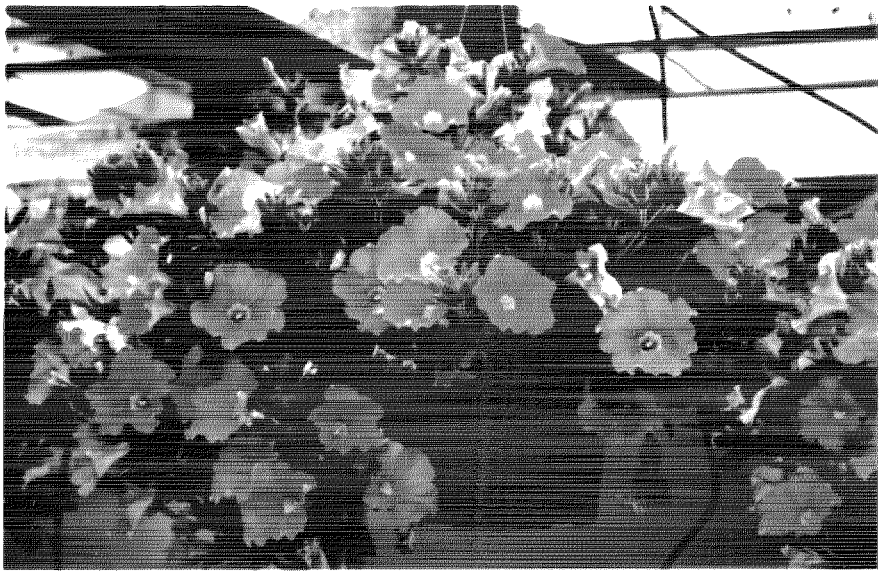

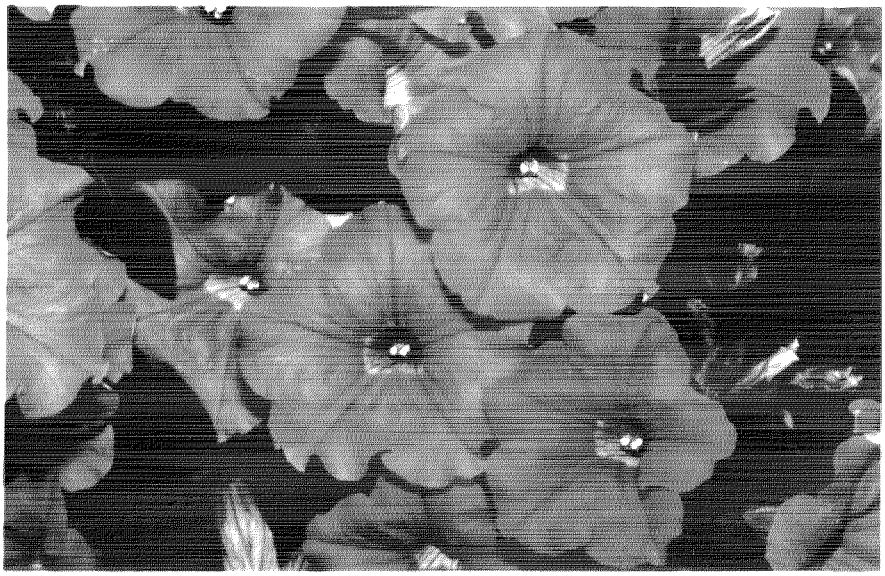

* * * * *